(12) United States Patent
Zhang et al.

(10) Patent No.: US 10,151,671 B2
(45) Date of Patent: Dec. 11, 2018

(54) SAMPLING DEVICE AND GAS CURTAIN GUIDE

(71) Applicant: Nuctech Company Limited, Beijing (CN)

(72) Inventors: Qingjun Zhang, Beijing (CN); Yuanjing Li, Beijing (CN); Zhiqiang Chen, Beijing (CN); Huishao He, Beijing (CN); Qiufeng Ma, Beijing (CN); Ziran Zhao, Beijing (CN); Yinong Liu, Beijing (CN); Yaohong Liu, Beijing (CN); Weiping Zhu, Beijing (CN); Xiang Zou, Beijing (CN); Jianping Chang, Beijing (CN)

(73) Assignee: Nuctech Company Limited, Beijing (CN)

( * ) Notice: Subject to any disclaimer, the term of this patent is extended or adjusted under 35 U.S.C. 154(b) by 115 days.

(21) Appl. No.: 15/238,598

(22) Filed: Aug. 16, 2016

(65) Prior Publication Data
US 2016/0356679 A1    Dec. 8, 2016

Related U.S. Application Data

(63) Continuation of application No. PCT/CN2015/098691, filed on Dec. 24, 2015.

(30) Foreign Application Priority Data

Dec. 31, 2014 (CN) .......................... 2014 1 0855315

(51) Int. Cl.
*G01N 1/24* (2006.01)
*G01N 30/30* (2006.01)
*G01N 1/22* (2006.01)

(52) U.S. Cl.
CPC ............. *G01N 1/24* (2013.01); *G01N 1/2211* (2013.01); *G01N 30/30* (2013.01)

(58) Field of Classification Search
CPC ......... G01N 1/24; G01N 1/2211; G01N 30/30
(Continued)

(56) References Cited

U.S. PATENT DOCUMENTS 5,011,517 A    4/1991 Cage et al.
2004/0227073 A1  11/2004 Krasnobaev et al.
(Continued)

FOREIGN PATENT DOCUMENTS

CN      201184853 Y    1/2009
CN      201561956 U    8/2010
(Continued)

OTHER PUBLICATIONS

International Search Report and Written Opinion dated Feb. 16, 2016 for PCT Application No. PCT/CN2015/098691 which corresponds in priority to above-identified subject U.S. application.

*Primary Examiner* — Walter L Lindsay, Jr.
*Assistant Examiner* — Ruth Labombard
(74) *Attorney, Agent, or Firm* — Knobbe Martens Olson & Bear LLP (57) ABSTRACT

A sampling device and a gas curtain guide are disclosed. In one aspect, the sampling device includes a chamber body. The chamber body includes a sample inlet, located at a first end of the chamber body, configured for suction of a sample. The chamber body further includes a sample outlet, located adjacent to a second end opposite to the first end of the chamber body, configured to discharge the sample. The chamber body further includes a gas inflation inlet, in a wall of the chamber body, configured to introduce a swirl gas flow into the chamber body. The chamber body further includes a gas exhaust opening configured to discharge gas (Continued)

so as to, together with the gas inflation inlet, generate a tornado type gas flow in the chamber body, which moves spirally from the first end to the second end of the chamber body.

19 Claims, 2 Drawing Sheets

(58) Field of Classification Search
USPC .................................................. 73/863.12
See application file for complete search history.

(56) References Cited

U.S. PATENT DOCUMENTS

| | | | |
|---|---|---|---|
| 2009/0050801 A1* | 2/2009 | Fedorov | H01J 49/066 |
| | | | 250/288 |
| 2011/0139902 A1 | 6/2011 | Atkinson et al. | |
| 2014/0116256 A1 | 5/2014 | Yamasaki et al. | |

FOREIGN PATENT DOCUMENTS

| | | |
|---|---|---|
| CN | 101936820 A | 1/2011 |
| CN | 102539514 A | 7/2012 |
| CN | 104517799 A | 4/2015 |
| CN | 104535379 A | 4/2015 |
| CN | 204314116 U | 5/2015 |
| CN | 204424206 U | 6/2015 |
| CN | 105203692 A | 12/2015 |
| DE | 199 26 285 A1 | 12/2000 |
| JP | 50-71386 A | 6/1975 |
| JP | 59-175157 U | 11/1984 |
| JP | 59-206741 A | 11/1984 |
| JP | 5-26790 A | 2/1993 |
| JP | 2011-247609 A | 12/2011 |

* cited by examiner

SAMPLING DEVICE AND GAS CURTAIN GUIDE

CROSS-REFERENCE TO RELATED APPLICATIONS

This application claims priority to International Application No. PCT/CN2015/098691, filed on Dec. 24, 2015, entitled "SAMPLING DEVICE AND GAS CURTAIN GUIDE", and Chinese Application No. 201410855315.4, filed on Dec. 31, 2014, incorporated herein by reference in their entirety.

BACKGROUND

Field

The disclosed technology relates to gas-borne substance detection and in particular to a tornado type sampling device and a gas curtain guide. The gas-borne substances sampled and detected include volatile organic compounds (VOCs), semi-volatile organic compounds (semi-VOCs), and surface contaminants.

Description of the Related Technology

Gas chromatography-ion mobility spectrometry (GC-IMS) combination technology has rapidly developed recently, with improved miniaturization, portability, high-speed analysis and the like. GC-IMS will be an important technology in the future for gas-borne substance detection systems to improve safety at airports, public transit systems, stadiums, and for shipping containers, for example.

When detecting gas-borne substances using rapid GC-IMS, a sample is first passed through a sampling device. Sampling directly affects the application, response sensitivity, efficiency, and detection performance. Existing sampling approaches for ion mobility spectrometry (IMS) include wipe sampling methods and direct suction-in methods.

Direct suction-in methods bring a sampling feeding inlet close to a sample and directly suction in the sample through a gas path structure with a pump so that the sample molecules are fed into the IMS apparatus for analysis. Wipe sampling methods apply flexible, high-temperature resistant wiping paper to an object to be analyzed, bring the wiping paper into a slot of a thermal desorption sample feeder, and heat the wiping paper to desorb the sample attached onto the wiping paper for analysis. However, the above sampling methods are not adequate for many security applications due to low sampling efficiency or relatively low sensitivity through a direct gas suction-in process. They may only sample surface contaminants and not volatile or semi-volatile organic compounds.

The disclosed technology includes a truncated cone type tornado generator to produce an artificial funnel-shaped tornado similar to that found in nature. As gas pressure in a swirl center of the tornado is 10 times lower than that in the periphery, the truncated cone type tornado generator achieves a strong suction effect and amplifies collection of gas-borne substances, such as VOCs, Semi-VOCs, and surface contaminants. The disclosed sampling device may be more efficient than direct gas suction methods. Therefore, it may be used for a sample feeder for IMS, GC, or rapid GC-IMS technology, achieving rapid on-site sampling and feeding of volatile, semi-volatile, and/or surface-contaminated trace substances without unpacking packages that carry the substances. The one-stop type detection technology may not only improve detecting speed but also avoid disputes on individual privacy during safety detection. Further, as it works like a sniffer dog, the apparatus and method are highly suitable for on-site rapid check in airports, customs house or the like.

SUMMARY OF CERTAIN INVENTIVE ASPECTS

The disclosed technology includes sampling devices and gas curtain guides that overcome at least some of the above disadvantages of existing sampling devices and methods.

The disclosed technology includes sampling devices and a gas curtain guides which may achieve amplified collection of gas-borne substances. The gas-borne substances include volatile organic compounds (VOCs), semi-volatile organic compounds (semi-VOCs), and surface contaminants. Applications include detecting air-borne substances in packages or contaminants on surfaces of packages, for rapid and highly effective inspection without unpacking.

One aspect is a sampling device. The sampling device includes a chamber body. The chamber body includes a sample inlet that is located at a first end of the chamber body and is configured for suction of a sample. The chamber body further includes a sample outlet, located adjacent to a second end opposite to the first end of the chamber body, configured for discharge of the sample. The chamber body further includes a gas inflation inlet configured to induct a flow of gas into the chamber body, and a gas exhaust opening configured to discharge the gas so as to, together with the gas inflation inlet, generate a tornado type gas flow in the chamber body, which travels spirally from the first end to the second end of the chamber body.

In an embodiment, a section of the chamber body has an inner wall with a truncated conical shape, the truncated conical shaped inner wall having a smaller-diameter round end adjacent to the sample inlet and a larger-diameter round end adjacent to the sample outlet of the chamber body.

In an embodiment, the gas inflation inlet is configured such that an axial gas introduction direction of the gas inflation inlet is approximately tangent to an inner surface of the inner wall of the chamber body but is inclined towards a side of the sample outlet.

In an embodiment, the gas exhaust opening is configured to discharge a peripheral gas of the tornado type gas flow formed within the chamber body.

In an embodiment, an opening direction of the gas exhaust opening is close to a direction that is opposite to a velocity direction of the gas flow at the gas exhaust opening.

In an embodiment, the sampling device further includes a mixing chamber body section provided at the second end of the chamber body. In an embodiment, the sample is fed into the mixing chamber body section and then into a detection system through a sample feeding opening.

In an embodiment, the mixing chamber body section is separated from other sections of the chamber body via a semi permeable membrane.

In an embodiment, the mixing chamber body section is provided with a carrier gas passage through which a carrier gas is injected into the mixing chamber body section for being mixing with the sample.

In an embodiment, the sampling device further includes a filter screen located at the first end and adapted for preventing large particle substances from entering the sample inlet. In an embodiment, the filter screen includes a rigid coarse filter screen for filtration of large particles and a fine filter screen for filtration of fine particles.

In an embodiment, the sampling device further comprises a temperature-controlling system adapted for controlling a temperature within the chamber body, and the temperature-controlling system comprises a heater and a temperature sensor.

In an embodiment, the sampling device further includes a thermal insulation layer surrounding a wall of the chamber body.

In an embodiment, the sampling device further includes a gas inflator pump in fluid communication with the gas inflation inlet and a gas exhaust pump in fluid communication with the gas exhaust opening, and, a flow rate of the gas exhaust pump is ten times or higher than that of the gas inflator pump.

Another aspect is a sampling device. The sampling device includes a gas guide chamber having a cylindrical inner wall. The sampling device further includes an end cap configured to seal a first end of the sampling device and having a sample inlet for suction of a sample. The sampling device further includes a gas curtain guide disposed near the sample inlet at the first end of the sampling device and engaged with the gas guide chamber, the gas curtain guide being configured with an inflation inlet for blowing gas into the sampling device so as to generate a tornado type gas flow in inner space within the gas curtain guide and the gas guide chamber.

In an embodiment, the gas curtain guide has a truncated conical shape inner wall and the sample inlet of the sampling device is located adjacent to a smaller-diameter round end of the truncated conical shape inner wall while is far away from a larger-diameter round end thereof.

In an embodiment, the gas curtain guide has a plurality of swirl gas holes, each of which has axial gas introduction direction approximately tangent to the inner wall of the gas curtain guide and inclined toward a direction away from a side of the sample inlet.

In an embodiment, the gas guide chamber further includes a gas exhaust opening provided in the inner wall of the gas guide chamber and away from the first end for discharging a periphery gas of the tornado type gas flow generated within the gas guide chamber.

In an embodiment, an opening direction of the gas exhaust opening is close to a direction that is opposite to a velocity direction of the gas flow at the gas exhaust opening.

In an embodiment, the sampling device further comprises a mixing chamber body section provided at the second end of the chamber body. In an embodiment, the sample is fed into the mixing chamber body section and then into a detection system through a sample introduction opening.

In an embodiment, the mixing chamber body section is separated from other sections of the chamber body via a semi permeable membrane.

In an embodiment, the mixing chamber body section is provided with a carrier gas passage through which a carrier gas is injected into the mixing chamber body section for being mixing with the sample.

In an embodiment, the sampling device further includes a filter screen located at the first end and adapted for preventing large particle substances from entering the sample inlet. In an embodiment, the filter screen includes a rigid coarse filter screen for filtration of large particles and a fine filter screen for filtration of fine particles.

In an embodiment, the sampling device further includes a temperature-controlling system adapted for controlling a temperature within the chamber body. In an embodiment, the temperature-controlling system includes a heater and a temperature sensor.

In an embodiment, the sampling device further includes a thermal insulation layer surrounding the wall of the chamber body.

In an embodiment, the sampling device further includes an inflator pump in fluid communication with the gas inflation inlet and an exhaust pump in fluid communication with the gas exhaust opening, and, a flow rate of the exhaust pump is ten times or higher than that of the inflator pump.

In an embodiment, the gas curtain guide defines an annular space configured to receive gas to generate gas pressure within the annular space and inflate gas into the interior space of the sampling device through the gas inflation inlet.

Another aspect is a gas curtain guide used in the above-mentioned sampling device. The gas curtain guide includes a gas inflation inlet for blowing gas into the sampling device so as to generate a tornado type gas flow in interior spaces of the gas curtain guide and the gas guide chamber. The gas curtain guide further includes a truncated conical shaped inner wall. The sample inlet of the sampling device is located adjacent to a smaller-diameter round end of the truncated conical shaped inner wall and away from a larger-diameter round end of the truncated conical shaped inner wall. The gas curtain guide defines an annular space configured to receive gas to generate a gas pressure within the annular space and inflate gas into the interior space of the sampling device through the gas inflation inlet.

DETAILED DESCRIPTION OF CERTAIN EMBODIMENTS

Although the disclosed technology is subject to various modifications and alternatives, exemplary embodiments of the disclosed technology will be shown as examples in the attached drawings and be described herein in detail. It should be understood that, however, the attached drawings and the detailed description are not intended to limit the disclosed technology to the embodiment set forth herein, rather, are intended to cover all the modifications, equivalents and alternatives fallen into the principles and spirit of the disclosed technology, the scope of which is defined in the claims. The attached drawings are provided for illustration purpose, and are not drawn to scale.

Several embodiments of the disclosed technology will be explained with reference to the attached drawings.

Figure 1:
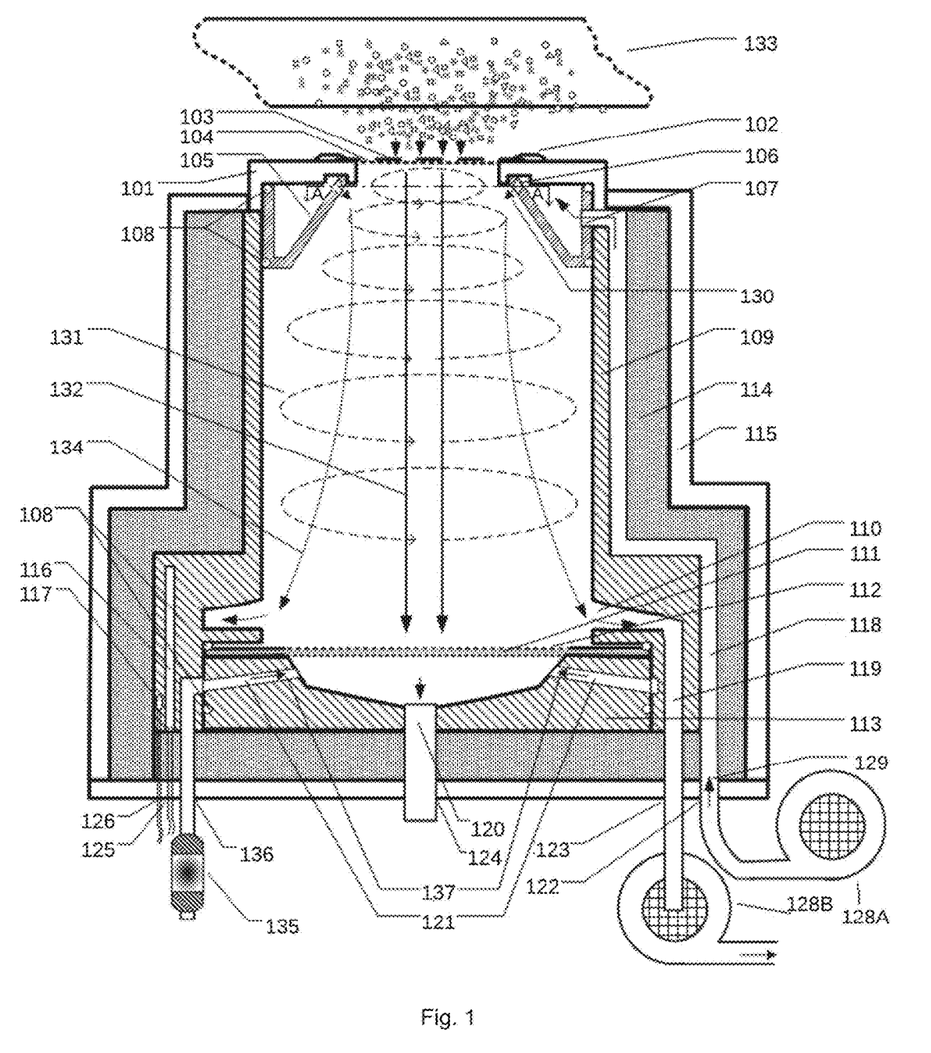
FIG. 1 is a sectional view of a sampling device according to an embodiment of the disclosed technology.

FIG. 1 is a longitudinal cross sectional view of a tornado type sampling device for sampling gas-borne (air-borne) substances including volatile organic compounds (VOCs), semi-volatile organic compounds (semi-VOCs), and surface contaminants. The tornado type real-time sampling device of FIG. 1 includes an end cap 101 having an aperture and a clamping ring 102 disposed on the end cap 101. A coarse filter screen 103 and a fine filter screen 104 are mounted over the aperture of the end cap 101 by the clamping ring 102 to prevent large particle substances from entering the sampling device. The coarse filter screen 103 filters out large particles, and is sufficiently rigid to bear external environment pressure and the impact of large particles. The fine filter screen 104 filters out fine solid particles or micro particles. Alternatively, an integrated end cap 101 having an aperture, also called a sample inlet, may be used. A porous element, such as coarse filter screen 103 or fine filter screen 104 is arranged over the sample inlet to prevent large particle substances from passing through the end cap 101.

The sampling device of FIG. 1 further includes a rotary gas curtain guide 105 over which the end cap 101 is closed and sealed through an O-type sealing ring 108 such that an upper annular surface is sealed by the end cap 101. The rotary gas curtain guide 105 has a cylindrical outer wall and also an inner wall having a cross section, for example, of a funnel type shape, as shown. In other words, the gas curtain guide 105 may be a combination of a barrel and a funnel type inner wall therein. Alternatively, the gas curtain guide 105 may be an integrally formed single piece. An angle between the funnel type inner wall and the cylindrical outer wall may be 20°~30°, although other values of the angle may be adopted. A diameter of the lower end face of the funnel type inner wall of the gas curtain guide 105 is at least two times of a diameter of the upper end face thereof. In other words, the diameter of a lower opening formed by the funnel type inner wall is at least two times of the diameter of an upper opening formed by the funnel type inner wall. This funnel-type design helps to simulate generation of a tornado within the sampling device. An interior space is defined by an inner surface of the funnel type inner wall of the gas curtain guide 105, that is, the interior space is defined between two inner wall sections of the gas curtain guide 105 as shown in the sectional view of FIG. 1.

Figure 2:
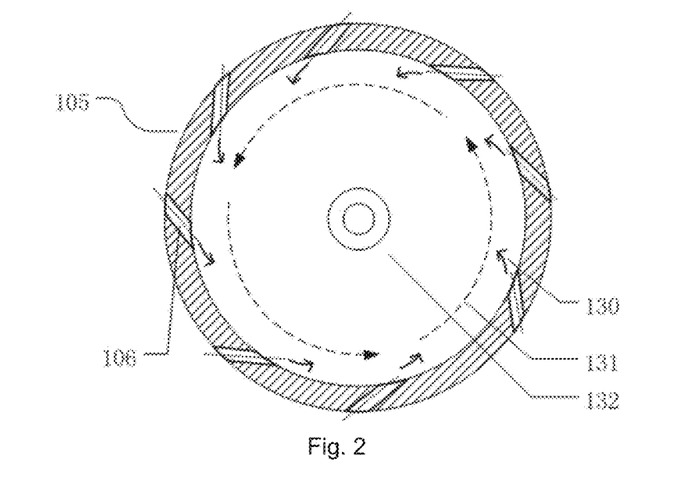
FIG. 2 is a sectional view of a gas curtain guide according to an embodiment of the disclosed technology.

FIG. 2 shows a schematic cross-sectional view of the side wall of the gas curtain guide 105 along line A-A. As shown in FIG. 2, a plurality of swirl gas holes 106 are formed evenly in the upper end of the funnel type inner wall of the gas curtain guide 105 and have their axial directions close to being tangent with the funnel type inner wall, and an angle of an axial line of the swirl gas hole 106 relative to a vertical direction is 45°~90°. Thereby, the swirl gas holes are tangent with the funnel type inner wall of the gas curtain guide 105 and face downward (in an arrow direction shown in FIG. 1), such that the gas may flow out from the swirl gas holes 106 and then flow downward in a direction that is tangent with the funnel type inner wall.

Referring to FIG. 1, gas inflation inlet 107 is formed in the cylindrical outer wall of the gas curtain guide 105. An annular space is defined by the cylindrical outer wall, the funnel type inner wall and the end cap 101 of the rotary gas curtain guide 105. Gas may enter the annular space through the gas inflation inlet 107, and then the gas within the annular space is blown into the funnel type interior space of the gas curtain guide 105 through the swirl gas holes 106 in the funnel type inner wall, generating a swirl gas curtain 130.

In this embodiment, the sample is suctioned at the upper end, discharged at the lower end and a flow of inflation gas flows from in the downward direction of the arrows spirally. However, this is only one example. When the sampling device is horizontally placed to face an object to be detected, for example, the sample inlet is placed to face the object to be detected which is located at the left of the sampling device, such that the side of the gas curtain guide 105 where the inlet is provided faces the left object to be detected, the funnel type inner wall is arranged transversely and the sample travels from the left to the right.

The gas curtain guide 105 may include a gas inflation passage 118. FIG. 1 shows an arrangement in which one end of the inflation passage 118 is in fluid communication with the gas inflation inlet 107 while the other end is communicated with a gas inflator pump 128A for gas inflation. The gas inflator pump 128A delivers the gas into the annular space through the inflation passage 118 and the gas inflation inlet 107, and the gas that enters the annular space is blown into the funnel type interior space through the swirl gas holes 106 of the funnel type inner wall, to form a swirl gas curtain 130.

The sampling device further includes a gas guide chamber 109 having a cylindrical inner wall. The gas guide chamber 109 is embedded into the sampling device under the gas curtain guide 105 by using an O-ring seal. The gas guide chamber 109 may be engaged with the gas curtain guide 105 in any other manner as long as the generation of a tornado type gas flow within the gas guide chamber is not affected. The tornado type gas flow is known to those skilled in the art. That is, peripheral portions of the gas flow in a spiral rotation at a high speed, or at least quickly, to rotate in a horizontal cross-section of the gas flow (in a cross-section of the gas guide chamber in this embodiment) while moving forward (from the end of the sample inlet to the end of the sample outlet, for example towards sample feeding opening 120) in a longitudinal direction, and at the same time, a center portion of the gas flow or a portion of the gas flow at its axis is suctioned forward in the longitudinal direction. The gas guide chamber 109 is configured for maintaining a tornado type cyclone and guiding gas-borne substances, such as VOCs, Semi-VOCs, or surface contaminants suctioned along the axis, to enter a subsequent detection device. As shown in FIG. 1, the swirl gas curtain 130 moves downward, and enters the gas guide chamber 109 to form a swirl gas flow 131. A tornado type swirl gas flow 132 flows in the gas guide chamber 109, passes through gas exhaust opening 110 at a lower side wall of the gas guide chamber 109, and then is discharged (e.g., through passage 119) through an exhaust pump interface 123 and a ventilation outlet 127.

The sampling device further includes a funnel type bottom cap 113 by which a lower end face of the gas guide chamber 109 is covered with an O-ring seal 108. A semipermeable membrane 111 is provided between the bottom cap 113 and the lower end opening of the gas guide chamber 109, and is provided for preventing water molecules, ammonia molecules and other contaminants in the suctioned gas-borne substance, such as VOCs, or Semi-VOCs, or surface contaminants, from entering and contaminating subsequent chromatographic column(s) or migration tube(s). In addition, the semipermeable membrane 111 may further restrict formation of cluster, thereby improving a resolution ratio of the instrument.

In an embodiment, there may be two mesh metal pieces 112, for clamping the semipermeable membrane 111 therebetween and protecting it from being broken due to impact of the gas flow.

The funnel type bottom cap 113 may form a mixing region or a mixing chamber for the carrier gas and the sample. The funnel type bottom cap 113 may comprises a carrier gas passage 121 for introduction of the carrier gas. The introduced carrier gas is mixed sufficiently with the sample in the funnel. The funnel type bottom cap 113 may further include a sample feeding opening 120 through which the collected sample and the carrier gas are discharged after, such as, being mixed and preheated. In some cases, the carrier gas and the sample may be discharged after being mixed directly without preheating.

The sampling device further comprises a temperature controlling system including a thermal insulation layer 114 provided on the gas guide chamber 109, and a heating rod (heater) 116 and a temperature sensor 117 provided within the gas guide chamber 109, and configured to control temperature of the gas guide chamber 109, for example, by heating up. The temperature controlling system may control the temperature inside the chamber in a range of 50° C.~250° C., which helps to quickly gasify high boiling gas-borne substance, such as VOCs, or Semi-VOCs, or surface contaminants so that it smoothly passes through the semipermeable membrane, and which also helps to sufficiently mix the gasified sample and the carrier gas entered from the carrier gas passage 121 in the funnel type side wall, effectively improving a detection limit of the instrument on high boiling substrate. After being mixed and preheated with the carrier gas, the collected sample may be brought into the sample feeding opening 120 by the carrier gas. In an embodiment of the present disclosure, the rotary gas curtain guide 105, the gas guide chamber 109 and the bottom cap 113 may be made of metallic materials with good thermal performance. In addition, the thermal insulation layer 114 may be made of aerogel or glass or ceramic wool which has a thickness of about 10 mm. Optionally, Teflon outer casing housing 115 may cover the outside the thermal insulation layer 114.

Figure 3:
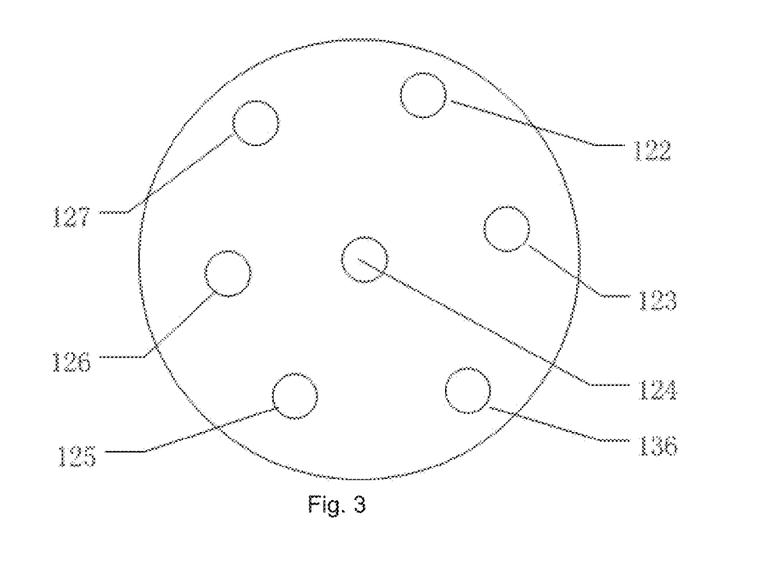
FIG. 3 is a bottom view of an outer cover of a sampling device according to an embodiment of the disclosed technology.

The bottom end face of the outer casing housing 115 may be provided with an inflator pump interface 122, an exhaust pump interface 123, a GC column/ion migration tube interface 124, a heating rod leading-out wire 125, a temperature sensor leading-out wire 126, a ventilation outlet 127 and a carrier gas tube interface 136, as shown in FIG. 3 in cross section and longitudinally in FIG. 1. The inflator pump interface 122 and the exhaust pump interface 123 may be connected respectively with a gas pump for continuously supplying a gas pressure so that a tornado type gas flow may be formed inside the sampling device. In an embodiment, the exhaust pump interface 123 is arranged to make the gas resistance as small as possible, so that the opening of the exhaust pump interface in the gas guide chamber faces toward a direction of gas flow, facilitating an easy inflow of the gas flow into the exhaust pump interface. The exhaust pump interface 123 may not be connected to the gas exhaust pump 128B and be served directly as a ventilation outlet. In order to discharge the suctioned and amplified tornado type gas flow, several ventilation outlets 127 may be formed. The GC column/ion migration tube interface 124 may be connected to a GC column or an ion migration tube. The carrier gas tube interface 136 may be connected to a molecular sieve 135 so that the carrier gas will be purified.

Power of the gas inflator pump 128A or gas exhaust pump 128B as shown may be adjusted as needed. Since the tornado type gas flow has a gas collection and amplification function, a flow rate of the gas exhaust pump 128B is ten times or more of that of the gas inflator pump 128A.

In order to prevent the interference of a gas flow from the gas inflator pump 128A on the target components suctioned from the sampled object 133, on one hand, a gas source for collection of the inflator pump is provided as far as possible from the sampled object 133, for example, by separating the pump from the sampling end holes by using a retractable and turn-able flexible conduit; on the other hand, the gas entering the inflator pump is filtered and purified, avoiding cross contamination of the gas and improving sensitivities of locating and sampling performance of the sampling instrument.

Sampling and feeding processes of the tornado type sampling device, which has a gas collection and amplification function, according to an embodiment of the disclosed technology will be described hereafter.

Front end opening/aperture of the sampling device according to the disclosed technology is placed near an object 133 to be sampled, that is, in a location that is away from the object by 5-10 cm, to aim at the object 133, while the gas pump and the gas exhaust pump 128B are turned on. The inflation gas flow 129 is inflated through an inflation tube into the annular space of the gas curtain guide 105 via the gas inflation inlet 107. A gas pressure is generated within the annular space under the action of a gas pressure continuously applied by the gas inflator pump 128A. With the action of the gas pressure, the gas is blown into interior space of the funnel through the swirl gas holes 106 of the gas curtain guide 105. Due to construction of the swirl gas holes 106, the gas is blown into the interior space in a predefined direction, forming a funnel type swirl gas curtain 130. In a case that the gas is constantly blown by the gas inflator pump 128A, the rotary gas curtain formed continuously moves along the inner wall of the gas guide chamber 109, that is, it rotates quickly around a central axis of the gas guide chamber 109 while moving downward, to form a tornado type gas flow 131. Under the action of a centrifugal force caused by this rotation, a central gas pressure of the tornado type gas flow reduces dramatically; for example, the gas pressure at the central axis 132 is ten times smaller than ambient pressure. Therefore, a great suction force may be generated at the central axis of the gas guide chamber 109. The suction force makes the gas-borne substance, such as VOCs, Semi-VOCs, or surface contaminants in the vicinity of the sampled object 133 to be suctioned in and adjacent to the center of the wind axis within the gas guide chamber 109 from a region around the front end aperture of the gas guide chamber 109, and to form a sample gas column that moves downward along a central axis of the tornado type gas flow and finally reaches the sample-supplying semipermeable membrane 111. This process is similar to a tornado phenomenon of "tornado suction-in water" in nature.

On one hand, the collected sample enters a funnel chamber of the bottom cap 113 through the semipermeable membrane 111, and is quickly gasified under a preheated condition and then is mixed sufficiently with the carrier gas flow 137 entered from the carrier gas passage 121 in the side wall of the bottom cap 113. After that, the carrier gas carrying the sample enters the sample-feeding opening 120.

On the other hand, a cyclone is formed at the periphery of the tornado type gas flow 131 forms the gas at the periphery of a rotation center of the tornado type gas flow 13 land moves along the side wall of the gas guide chamber 109. At the bottom of the gas guide chamber, gas of the peripheral cyclone enters the gas exhaust opening 110 and forms a vortex flow 134 that will be discharged through the ventilation outlet 127. The gas exhaust opening 110 is oriented towards a gas flow direction of the cyclone. In the orientation shown in FIG. 1, the gas exhaust opening 110 may be inclined upward, and, the outlet may deviate towards a tangential direction of the inner wall, instead of being oriented towards a center of the chamber body, facilitating the opening direction of the outlet to be much closer to the velocity direction of the gas flow at the outlet. That is to say, although the opening direction of the gas exhaust opening 110 is not strictly opposite to the velocity direction of the gas flow at the outlet, it is close to a direction opposite to the velocity direction of the gas flow at the outlet, such that the gas will enter more easily the gas exhaust opening 110 and is discharged.

Through this process, the sampling device may constantly suction sample molecules, thereby achieving amplified collection of the gas-borne substance, such as VOCs, or Semi-VOCs, or surface contaminants.

This tornado type real-time sampling device having the gas amplified collection function may be used directly as a sample feeder of analytical instruments including IMS, GC, MS, GC-IMS, and GC-MS.

Another embodiment of the sampling device according to the disclosed technology will be described hereafter. This embodiment is similar to those mentioned in the above, and only different parts will be described for clarity.

In this embodiment, the sampling device includes a first end and a second end opposite to the first end. The sampling device includes a chamber body, and a part 105 of the chamber body has a funnel shape or a truncated conical shape. Specifically, the chamber body has a sample inlet that is adjacent to the first end and is configured for suction of the sample, and a sample feeding opening 120 that is adjacent to the second end and is configured for discharge of the sample. The sample inlet of the chamber body is located adjacent to a smaller-diameter round end of the truncated conical shaped inner wall, and the larger-diameter round end of the truncated conical shaped inner wall is close to the sample outlet.

In other words, the smaller-diameter end of the funnel type inner wall of part 105 will face the sample, while the larger-diameter end faces towards the sample outlet for discharging the sample. It should be noted that the chamber body shown in FIG. 1 is oriented such that the sample inlet faces upwards while the sample outlet for discharging the sample faces downwards, that is, the funnel type chamber body is arranged in an inverted funnel manner. However, it is only an example. When the sampling device is horizontally placed to face an object to be detected, for example, the sample inlet is placed to face the object to be detected which is located at the left of the sampling device 100 and a side of the funnel type inner wall where the smaller opening is provided faces the object to be detected at the left, such that the funnel type inner wall is placed in a horizontal arrangement manner.

The chamber body is further formed with a gas inflation inlet 107 configured to introduce a flow of gas into the chamber body, in order to form a tornado type gas flow within the chamber body. The chamber body is further formed with a gas exhaust opening configured to discharge the gas and to, together with the gas inflation inlet 107 in the chamber body, generate the tornado type gas flow in the chamber body. Specifically, the gas inflation inlet 107 is configured such that an axial gas introduction direction of the gas inflation inlet 107 is approximately tangent to an inner surface of the inner wall of the chamber body but is inclined towards a side of the sample outlet, as shown in FIG. 2.

In this embodiment, the gas curtain guide 105 may not be provided alone, and, an arrangement in which the abovementioned gas inflation inlet 107 and a corresponding gas inflation passage are provided in the inner wall of the chamber body adjacent to the sample inlet will achieve a similar effect as that of the abovementioned gas curtain guide 5. Moreover, an annular space for the gas curtain guide, as mentioned in the aforementioned embodiment, may be formed inside the chamber body, and is configured to accommodate the gas therein to create a gas pressure within the annular space, and, the gas is inflated into the interior space of the sampling device through the gas inflation inlet.

The gas exhaust opening 110 is located in wall of the chamber body, and may be arranged in a similar manner to the gas exhaust opening in the aforementioned embodiment of the disclosed technology. The gas exhaust opening 110 faces toward the tornado type gas flow spirally advanced from the gas inflation inlet 107 so that the gas flow enters the gas exhaust opening 110 with the gas resistance as small as possible. The peripheral gas of the tornado type gas flow formed within the chamber body is discharged through the gas exhaust opening 110. The peripheral gas is not limited to be the gas, and it may contain small amount of the sample. An opening direction of the gas exhaust opening 110 is close to a direction opposite to the velocity direction of the gas flow at the gas exhaust opening 110.

The sampling device may further comprise a filter screen located at a first end side of the sample inlet and configured for preventing large particle substances from entering the sample inlet. The filter screen comprises a rigid coarse filter screen for filtration of large particles and a fine filter screen for filtration of fine particles.

The sampling device may further comprise a temperature-controlling system adapted for controlling a temperature within the chamber body, and the temperature-controlling system comprises a heater and a temperature sensor. The sampling device may further comprise a thermal insulation layer surrounding the wall of the chamber body. In this embodiment, the chamber body may be an integrated one, or may be an assembled one consisted of several components by means of welding, riveting, etc., which do not bring any substantial effect on the gas flow inside the chamber body.

The chamber body, in this embodiment, may be also provided with an end cap 101, filter screens 103, 104, gas inflator pump 128A and gas exhaust pump 128B, a sample-supplying semipermeable membrane 111, a temperature controlling system, a thermal insulation layer 114, etc., as those in the aforementioned embodiment. In this embodiment, the chamber body may further include a mixing region for mixing the carrier gas with the sample. That is, the mixing region is provided at a lower section of the chamber body and is separated, e.g., by the semipermeable membrane 111, from a section of the chamber body where the tornado type gas flow is formed. According to this embodiment, there may provide two mesh metal pieces 112, for clamping the semipermeable membrane 111 and protecting it from being broken due to an impact of the gas flow. The chamber body may comprise a carrier gas passage 121 at its lower section, which passage is provided for injection of the carrier gas which will be sufficiently mixed with the sample in the funnel. The chamber body may further comprise a sample feeding opening 120 at its lower section, through which the collected sample and the carrier gas are discharged after being mixed and preheated. Similarly, the bottom end face of the chamber body may be the same as that in the aforementioned embodiment of the disclosed technology, as shown in FIG. 3. The bottom end face of the chamber body may be provided with an inflator pump interface 122, an exhaust pump interface 123, a GC column/ion migration tube interface 124, a heating rod leading-out wire 125, a temperature sensor leading-out wire 126, a ventilation outlet 127 and a carrier gas tube interface 136. The inflator pump interface 122 and the exhaust pump interface 123 may be connected respectively with a gas pump, for example, a gas inflator pump 128A and gas exhaust pump 128B, for continuously supplying a gas pressure so that a tornado type gas flow is formed inside the sampling device, and, the flow rate of the gas exhaust pump 128B is ten times or more than the gas inflator pump 128A. In an embodiment, the exhaust pump interface 123 is arranged to make the gas resistance as small as possible, so the opening of the exhaust pump interface in the gas guide chamber is desired to face toward a flowing direction of the gas flow, facilitating an easy inflow of the gas flow into the exhaust pump interface. The exhaust pump interface 123 may not be connected to the gas exhaust pump 128B and be served directly as the ventilation outlet. In order to discharge the suctioned and amplified tornado type gas flow, several ventilation outlets 127 may be formed. The GC column/ion migration tube interface 124 may be connected directly to an ion migration tube. The carrier gas tube interface 136 is connected to a molecular sieve 135 so that the carrier gas will be purified.

In another embodiment of the sampling device according to the disclosed technology, a section of the chamber body has an inner wall with a partially spherical shape, instead of a truncated conical shape. That is to say, the inner wall of this section of the chamber body has such a cambered surface that a portion of the inner wall of the chamber body near the sample inlet has a smaller diameter while a portion of the inner wall of the chamber body near the sample outlet has a larger diameter, so that a tornado type gas flow will be formed inside the chamber body.

The previous description of the disclosed examples is provided to enable any person skilled in the art to make or use the present invention. Various modifications to these examples will be readily apparent to those skilled in the art, and the generic principles defined herein may be applied to other examples without departing from the spirit or scope of the invention. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope. Thus, the present invention is not intended to be limited to the examples shown herein but is to be accorded the widest scope consistent with the principles and novel features disclosed herein.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

What is claimed is:

1. A sampling device, comprising:
   a chamber body comprising:
      a sample inlet that is located at a first end of the chamber body and is configured for suction of a sample;
      a sample outlet that is located adjacent to a second end, opposite to the first end, of the chamber body and is configured for discharge of the sample;
      a gas inflation inlet, formed in a wall of the chamber body, configured to introduce a selected gas flow into the chamber body; and
      a gas exhaust opening, formed in the wall of the chamber body, configured to discharge gas so as to, together with the gas inflation inlet, generate a tornado type gas flow in the chamber body, which travels spirally from the first end to the second end of the chamber body,
      wherein, a section of the chamber body has an inner wall with a truncated conical shape, the truncated conical shaped inner wall having a smaller-diameter round end adjacent to the sample inlet and a larger-diameter round end adjacent to the sample outlet of the chamber body.

2. The sampling device of claim 1, wherein the gas inflation inlet is configured such that an axial gas introduction direction of the gas inflation inlet is tangent to an inner surface of the inner wall of the chamber body but is inclined towards a side of the sample outlet.

3. The sampling device of claim 1, wherein, the gas exhaust opening is configured to discharge a peripheral gas of the tornado type gas flow formed within the chamber body, and wherein an opening direction of the gas exhaust opening is opposite to a velocity direction of the gas flow at the gas exhaust opening.

4. The sampling device of claim 1, further comprising a mixing chamber body section provided at the second end of the chamber body, and the sample is fed into the mixing chamber body section and then into a detection system through a sample feeding opening.

5. The sampling device of claim 4, wherein the mixing chamber body section is separated from other sections of the chamber body via a semipermeable membrane.

6. The sampling device of claim 4, wherein the mixing chamber body includes a carrier gas passage through which a carrier gas is injected into the mixing chamber body section for being mixing with the sample.

7. The sampling device of claim 1, further comprising a temperature-controlling system adapted for controlling a temperature within the chamber body, the temperature-controlling system comprising a heater and a temperature sensor.

8. A sampling device, comprising:
   a gas guide chamber having a cylindrical inner wall;
   an end cap configured to seal a first end of the sampling device and having a sample inlet for suction of a sample,
   a gas curtain guide disposed near the sample inlet at the first end of the sampling device and engaged with the gas guide chamber, the gas curtain guide being provided with a gas inflation inlet for blowing gas into the sampling device so as to generate a tornado type gas flow in interior spaces of the gas curtain guide and the gas guide chamber.

9. The sampling device of claim 8, wherein the gas curtain guide has a truncated conical shaped inner wall, and wherein the sample inlet of the sampling device is located adjacent to a smaller-diameter round end of the truncated conical shaped inner wall and away from a larger-diameter round end of the truncated conical shaped inner wall.

10. The sampling device of claim 9, wherein the gas curtain guide has a plurality of swirl gas holes, each of which has axial gas introduction direction tangent to the inner wall of the gas curtain guide and being inclined toward a direction away from a side of the sample inlet.

11. The sampling device of claim 8, wherein the gas guide chamber further comprises a gas exhaust opening provided in the inner wall of the gas guide chamber and away from the first end for discharging a periphery gas of the tornado type gas flow generated within the gas guide chamber, an opening direction of the gas exhaust opening being opposite to a velocity direction of the gas flow at the gas exhaust opening.

12. The sampling device of claim 8, further comprising a mixing chamber body section provided at the second end of the chamber body, wherein the sample is fed into the mixing chamber body section and then into a detection system through a sample introduction opening.

13. The sampling device of claim 12, wherein the mixing chamber body section is separated from other sections of the chamber body via a semipermeable membrane.

14. The sampling device of claim 12, wherein the mixing chamber body section is provided with a carrier gas passage through which a carrier gas is injected into the mixing chamber body section for mixing with the sample.

15. The sampling device of claim 8, further comprising:
a temperature-controlling system adapted for controlling a temperature within the chamber body, wherein the temperature-controlling system comprises a heater and a temperature sensor.

16. The sampling device of claim 8, further comprising a thermal insulation layer surrounding a wall of the chamber body.

17. The sampling device of claim 8, further comprising:
a gas inflator pump in fluid communication with the gas inflation inlet; and
a gas exhaust pump in fluid communication with the gas exhaust opening, wherein a flow rate of the gas exhaust pump is ten times or higher than that of the gas inflator pump.

18. The sampling device of claim 8, wherein the gas curtain guide defines an annular space configured to receive gas to generate a gas pressure within the annular space and inflate gas into the interior space of the sampling device through the gas inflation inlet.

19. A gas curtain guide for use in the sampling device of claim 8, wherein the gas curtain guide comprises:
a gas inflation inlet for blowing gas into the sampling device so as to generate a tornado type gas flow in interior spaces of the gas curtain guide and the gas guide chamber; and
a truncated conical shaped inner wall, wherein the sample inlet of the sampling device is located adjacent to a smaller-diameter round end of the truncated conical shaped inner wall and away from a larger-diameter round end of the truncated conical shaped inner wall, wherein the gas curtain guide defines an annular space configured to receive gas to generate a gas pressure within the annular space and inflate gas into the interior space of the sampling device through the gas inflation inlet.

* * * * *